United States Patent [19]
Craighead

[11] Patent Number: 5,867,266
[45] Date of Patent: Feb. 2, 1999

[54] MULTIPLE OPTICAL CHANNELS FOR CHEMICAL ANALYSIS

[75] Inventor: Harold G. Craighead, Ithaca, N.Y.

[73] Assignee: Cornell Research Foundation, Inc., Ithaca, N.Y.

[21] Appl. No.: 632,329

[22] Filed: Apr. 17, 1996

[51] Int. Cl.[6] ................................................ G01N 21/01
[52] U.S. Cl. ...................... 356/344; 356/246; 204/603; 204/612
[58] Field of Search ................................. 356/344, 246; 204/451, 452, 455, 470, 601, 603, 605, 619, 620, 612

[56] References Cited

U.S. PATENT DOCUMENTS

| | | |
|---|---|---|
| 4,288,283 | 9/1981 | Umezaki et al. . |
| 4,634,495 | 1/1987 | Gobrecht et al. . |
| 4,802,951 | 2/1989 | Clark et al. . |
| 5,047,117 | 9/1991 | Roberts . |
| 5,078,833 | 1/1992 | Kadomura . |
| 5,205,902 | 4/1993 | Horton et al. . |
| 5,302,264 | 4/1994 | Welch et al. . |
| 5,350,499 | 9/1994 | Shibaike et al. . |
| 5,582,705 | 12/1996 | Yeung et al. ........................... 204/603 |

OTHER PUBLICATIONS

Stu Borman, "Developers of Novel DNA Sequencers Claim Major Performance Advances", Sci. Tech., Jul. 24, 1995, pp. 37–39.

*Primary Examiner*—F. L Evans
*Attorney, Agent, or Firm*—Jones, Tullar & Cooper P.C.

[57] ABSTRACT

Apparatus for optical analysis of a sample material includes a channel block incorporating microfabricated channels and an integral gel material. Illuminating optics direct light to the sample material and light reflected from, refracted by and/or emitted by the sample is collected by collection optics for detection. The gel material is formed within the channels and includes multiple closely spaced pillars to form a porous separator for sample material to be analyzed.

43 Claims, 7 Drawing Sheets

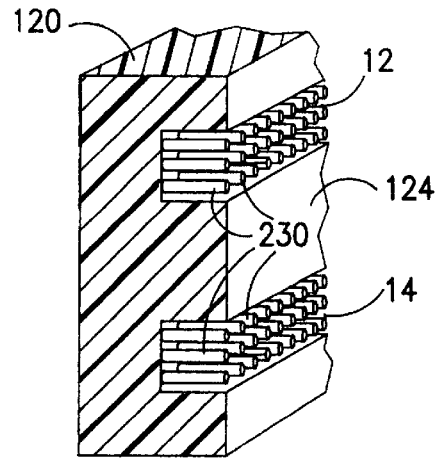
FIG. 7
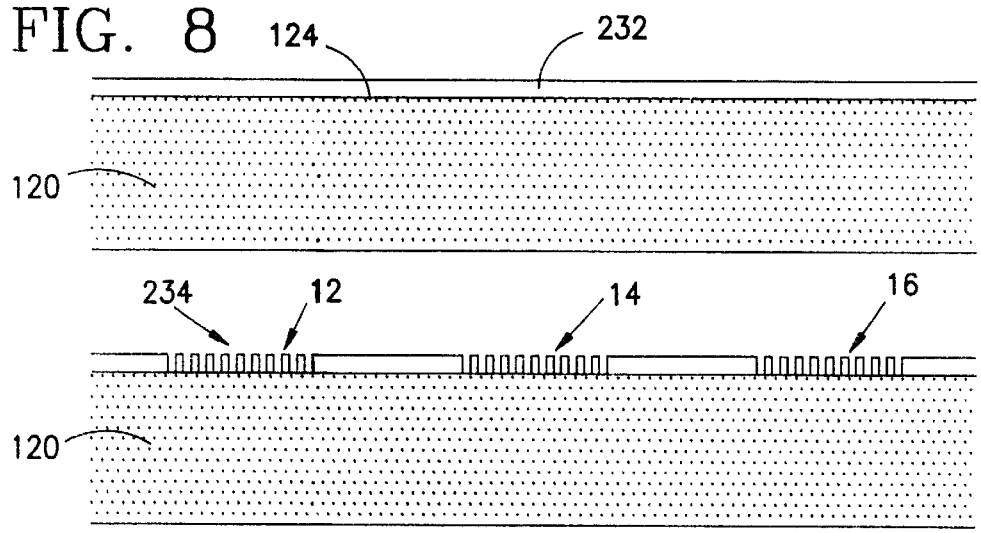
FIG. 8
FIG. 9
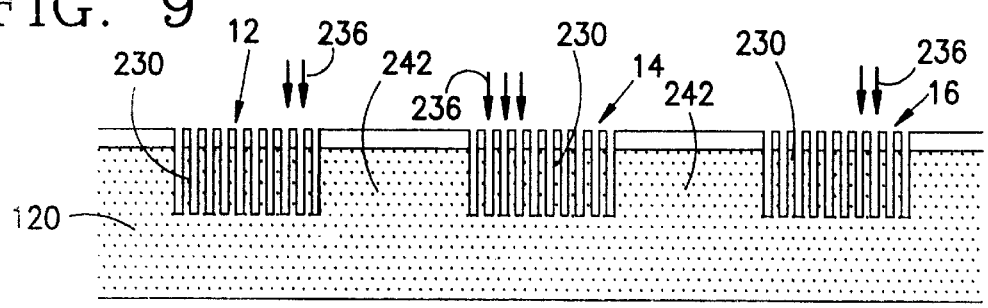
FIG. 10
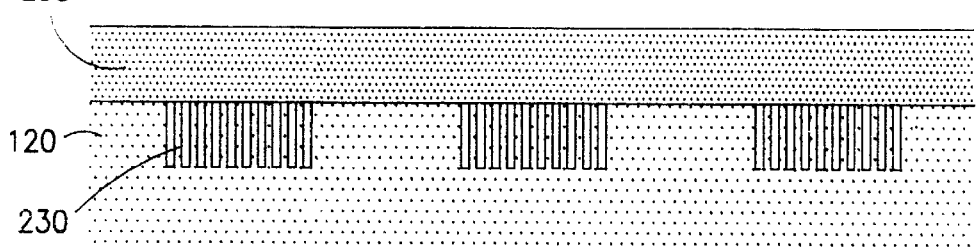
FIG. 11
1 μm

|— 1.00 μm —|

MULTIPLE OPTICAL CHANNELS FOR CHEMICAL ANALYSIS

BACKGROUND OF THE INVENTION

The present invention relates, in general, to a method and apparatus for analysis of chemical species separated by differences in flow rate through a porous medium, and, more particularly, to a method and apparatus for analysis of such species through optical absorption, reflection, refraction or fluorescence simultaneously in multiple micron-scale optical channels. The invention further relates to a microfabricated porous medium for such channels.

Optical systems for use in chemical analysis are well known, and the use of such systems in electrophoretic DNA sequencing is a particularly important application because of the intense interest in the sequencing of the human genome. This is a multiyear, multibillion dollar project which is directed to improving, if not revolutionizing, the ability to diagnose and treat illness.

Significant progress is being made in this field, and commercial optical systems are now available which are capable of sequencing DNA by gel electrophoresis of fluorescently labeled DNA fragments.

Because DNA sequencing is a highly complex procedure which requires a great deal of time and involves high cost, a considerable amount of research is being done into techniques and devices for reducing the time required for such sequencing, with one technique including the parallel reading of fluorescence from multiple capillaries. However, problems still remain in processing the DNA, in supplying it to the capillaries, in causing the DNA to pass through the capillaries, and in optically reading out the results, for currently available systems are relatively large, are expensive, and, although capable of operating faster than previous systems, still require very long time periods to sequence DNA fractions. Thus, the time required to sequence the three billion base pairs which comprise the human genome is still measured in years, and, there is an urgent need for an improved optical system for carrying out such procedures. Such an improved system would also have application in the analysis of other chemical species, particularly where the species are separated by differences in flow rate through a porous medium.

In electrophoretic analysis, chemical species are separated by an electric field which produces varying flow rates, and the separated products may then be detected optically. In typical DNA sequencing applications, the DNA fragments to be analyzed are added to a gel material which carries the fragments through electrophoresis channels. Such gels create problems, however, since it is difficult to fill narrow capillaries with the gel material, thereby increasing the time required and the expense of carrying out the sequencing process. Efforts have been made to develop an artificial gel material in the form of a porous medium, but the dimensions of such structures have been limited to those obtainable by photolithography. In addition, the production of artificial gel structures by such a process is too expensive for practical use. Thus, there is a need for an artificial gel structure which can be formed by processes that are easily carried out over large areas and which can be fabricated in inexpensive materials. Such a gel material would find wide use in a miniaturized, compact, and proportionately less expensive systems for chemical analysis.

SUMMARY OF THE INVENTION

Briefly, the present invention relates to a miniaturized optical system for chemical analysis and to a microfabricated gel material usable in such a miniaturized system. The invention utilizes multiple parallel microoptical illumination paths from one or more light sources leading to individual sample channels. The illumination from the light source may be divided and directed in parallel to corresponding channels, or may be a single beam scanned sequentially over the channels without a need for mechanically translatable optics or the need for moving the sample channels. Preferably, the illumination source is a laser.

Each optical path directs the illumination to a corresponding sample channel where components of the sample material to be detected may be caused to fluoresce, for example. Light emitted from the sample is collected and focussed onto a detector array which may include individual detectors for each sample channel, the detectors being responsive to selected wavelengths in the emitted light for identification of the sample material components. By using miniaturized optical components, illumination and collection lenses and other optical elements can be reduced to less than 1 mm diameter, and the illumination and collection path length can be reduced to a total of about 1 cm. An array of aspheric illumination and/or collection microlenses provides high optical efficiency and further provides a complete set of optics for each of the multiple sample channels.

By providing multiple sets of microptic illumination and collection paths and multiple sample channels, the structure is completely scalable without the need to extend the optical path length for any channel as the number of sample channels increases. Further, the microoptical system of the invention is easily mass produced by current commercial technologies, and in large quantities can be produced relatively inexpensively.

Preferably, the optical system incorporates a carrier block which incorporates a plurality of parallel sample channels. The carrier block may be replicated in optically clear plastic from a master die, as by a conventional molding process, to allow the sample channels to be readily produced with precise dimensions at a low cost so as to provide disposable sample holders. The block preferably is molded in two parts, one part, which may be referred to as the channel block, including the parallel sample channels on a first surface and the other part, which may be referred to as the cover block, providing a cover for the channels. If desired, channels or parts of channels, can be formed in both parts of the carrier block, with the channels being completed and enclosed when the two parts of the block are assembled.

In one form of the invention, one part of the carrier block, for example the channel block, may incorporate multiple miniaturized illuminating lenses on a second surface spaced from and parallel to the first surface on which the sample channels are located. Preferably one lens is provided for each channel, or for a small group of channels, for directing light from an external source such as a laser (or multiple lasers) through the channel block to the respective sample channels. The illuminating lenses are molded as an integral part of the channel block in a preferred form of the invention, although they may be adhesively secured to a surface of the channel block, if desired.

In this embodiment, the second part of the carrier block, for example the cover block, carries collection optics, preferably including a collection lens for each channel for collecting output light passing through, emitted by, or reflected from, sample material in the sample channels. The collection optics also preferably include diffraction elements, to separate the output light by wavelength, and directs this output light to suitable detectors. The collection optics preferably are molded as an integral part of the cover block, which also is optically clear plastic in the preferred form of the invention, this fabrication process enabling rapid and inexpensive replication of the cover block and optics.

The carrier block may incorporate suitable electrodes for supplying electric potentials to sample material in the sample channels, to permit electrophoretic analysis of this material. In this configuration the structure of the present invention is particularly advantageous when used in the fluorescent detection and analysis of sample material such as dye-labeled DNA fragments in electrophoretic DNA sequencing. Accordingly, the following description of preferred forms of the invention will be particularly directed to this process, although it will be understood that the described optical system lends itself to application in other analytical processes.

The carrier block is illuminated by a suitable light source such as a laser, although it may be utilized with other light sources such as solid state laser arrays. The light is directed, in the foregoing form of the invention, from a light source adjacent the second surface of the carrier block through the illumination optics on that surface and through the block to the sample channels. The light passes through the channels, with some of the light striking the sample material in those channels to cause fluorescence, for example. Fluorescent light emitted the first surface of the carrier block is directed by the output optics on the cover block to suitable detectors for measurement.

In another embodiment of the invention, the illumination and collection optics are on the same side of the carrier block, and are separated by a dichroic mirror. Illuminating light is directed onto the channels in the carrier block by the dichroic mirror to cause fluorescence in the sample material. Emitted fluorescence is directed back along the path of the illuminating light and passes through the dichroic mirror to a detector in this case, a single array of microlenses serves as both the illuminating and the collection optics.

The sample channels may incorporate a porous material for separating a sample material as it passes through the channel, for example under the influence of an electric field in an electrophoresis process. In the present invention, the porous material may be an artificial gel structure incorporated in, and fabricated at the same time as, the sample channels. The channels and the gel structure are fabricated by an etching process which produces a very narrow channel and a multiplicity of micron-scale, generally parallel, spaced pillars within this channel and perpendicular to the direction of motion of sample material to be analyzed. As noted above, the gel structure may be used as a die in a suitable glass or plastic master mold, and replicated in a conventional molding process to enable many copies to be made from a single mold by a simple, relatively inexpensive process. The copies preferably are formed of optically clear plastic.

When the above-described optical system is used in analysis of samples such as DNA fragments, the carrier block is fabricated with multiple parallel channels in the channel block portion, with the artificial gel structure incorporated in all of the channels. The samples, such as dye-labeled DNA fragments, are added to the channels and the channels are closed by the second, cover block portion of the carrier block. Thereafter the carrier block is placed between a laser light source and corresponding fluorescence detectors and an electric field is provided in each channel to separate the fragments in known manner. The illuminating light produces characteristic fluorescence in the separated dye-labeled sample fragments, so that parallel, and thus simultaneous, readings of the fluorescence of the DNA fragments are obtained in each of the channels.

The carrier blocks are easily replicated in plastic, glass or other transparent materials, and thus are inexpensive enough to allow disposability of the blocks to prevent contamination between samples. The small size also reduces the cost, and the geometry of the system allows simultaneous readouts to increase the speed of analysis.

BRIEF DESCRIPTION OF DRAWINGS

The foregoing, and additional objects, features, and advantages of the invention will be apparent to those skill in the art from the following detailed description of a preferred embodiment thereof, taken in conjunction with the accompanying drawings, in which:

FIG. 7 is an enlarged perspective view of a microfabricated flow channel incorporating an artificial gel usable in the optical system of the invention;

FIGS. 8–11 diagrammatically illustrate a process incorporating election beam lithography for microfabrication of sample channels incorporating the artificial gel of FIG. 7;

DESCRIPTION OF PREFERRED EMBODIMENT

Figure 1:
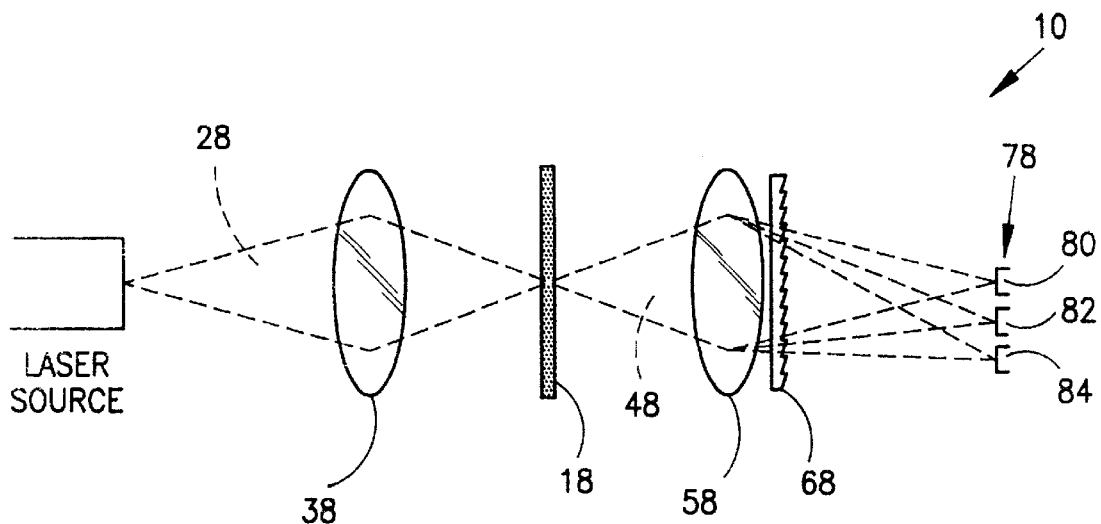
FIG. 1 is a diagrammatic end view illustration of a miniaturized optical chemical analysis system incorporating microfabricated flow channels, in accordance with the present invention.
Figure 2:
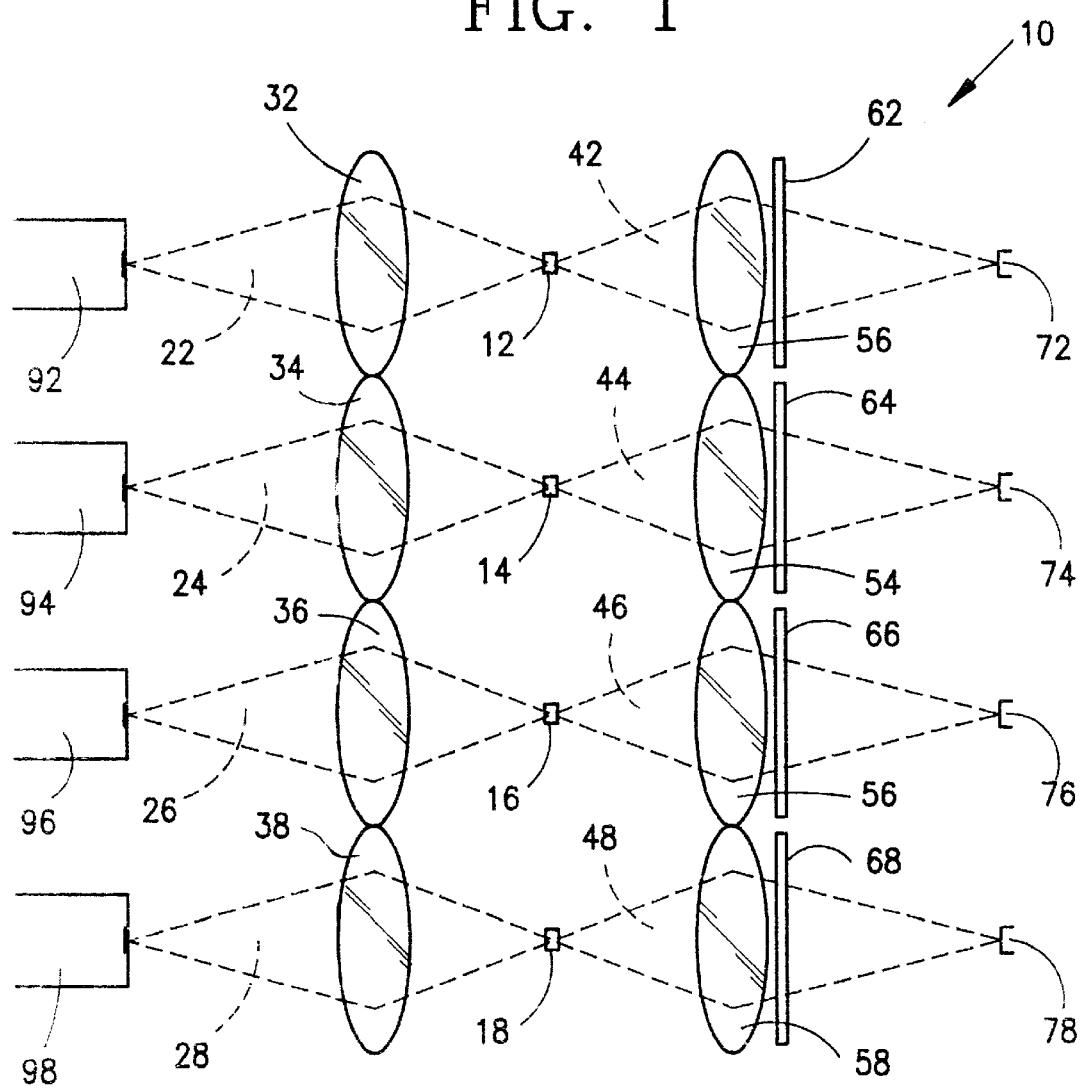
FIG. 2 is a diagrammatic top plan view of the system of FIG. 1, illustrating in diagrammatic form plural parallel microfabricated flow channels.

Turning now to a more detailed description of the present invention, FIGS. 1 and 2 illustrate in diagrammatic form a microlens array 10 for optical analysis of sample material located in a plurality of elongated, closely-spaced, generally parallel, coplanar sample channels 12, 14, 16 and 18. These channels may carry any desired chemical species for optical analysis, but for illustration, the sample material is described herein as including DNA fragments which are to be analyzed, or sequenced. The DNA fragments, in one embodiment, may be carried by a gel material which is injected into the respective sample channels. However, since currently available gels limit the DNA sequencing process because of the difficulty encountered in attempting to fill narrow capillary channels with the gel material, in accordance with the preferred form of the present invention the sample channels 12, 14, 16 and 18 are fabricated to include an artificial gel material, as will be described below.

Although four sample channels are illustrated, it will be understood that a large number of micro channels may be provided in order to improve the throughput of the samples being analyzed. These channels may be located in groups, may be evenly or irregularly spaced, as desired, and preferably are generally linear and parallel to each other. When the analysis involves DNA sequencing, the fragments are labeled with fluorescent dyes in order to permit optical detection, as is known. These fragments are fluoresced by impinging light from illumination laser beams 22, 24, 26 and 28 which are directed to corresponding sample channels by way of suitable illumination optics such as illumination microlenses 32, 34, 36 and 38. The laser beams are focused on the sample channels to cause the labeled fragments to fluoresce at known wavelengths. This produces corresponding output beams 42, 44, 46, and 48 which are directed by corresponding collection lenses 52, 54, 56 and 58 through wavelength separation optics such as diffraction gratings or prisms 62, 64, 66 and 68 which provide wavelength separation of each output beam, as best illustrated in FIG. 1. The separated wavelengths are directed to corresponding photo detectors 72, 74, 76 and 78, aligned with corresponding sample channels and their respective collection lenses and gratings. Each photo detector comprises a plurality of light sensitive elements such as the three elements 80, 82, and 84 illustrated in FIG. 1 as photo included in detector 78. Photodetectors 72, 74, 76 and 78 form an array of detector elements which measure the output light from corrresponding sample channels.

The illumination laser beams 22, 24, 26 and 28 may be generated by corresponding individual solid state or similar lasers such as those illustrated at 92, 94, 96 and 98, or may be from a single laser source having its output beam divided into plural illumination beams.

The optical system of FIGS. 1 and 2 permits measurements of the optical characteristics of a wide variety of sample materials. One example of such a measurement is the parallel sequencing of DNA fragments, which is carried out in the present device in a plurality of electrophoretic DNA sample channels for improved speed of processing. In accordance with this aspect of the present invention, a large number of very narrow sample channels, in the range of 1 mm or less in width and depth, are fabricated to incorporate a porous gel material which will receive the material to be analyzed. A simple photolithographic process is used to define the locations and dimensions of the channels, with the artificial gel material described herein permitting the channels to have dimensions 10–100 times smaller than was possible when prior conventional gel materials were used. Of course, if such a conventional gel material is to be used in the present optical system, the channels will be larger, but miniaturized channels in combination with the artificial gel are preferred. The preferred process for making the channels utilizes dry and isotropic ion etches, rather than wet chemical etches, to form the channels and to simultaneously fabricate the artificial gel within the channels.

Figure 3:
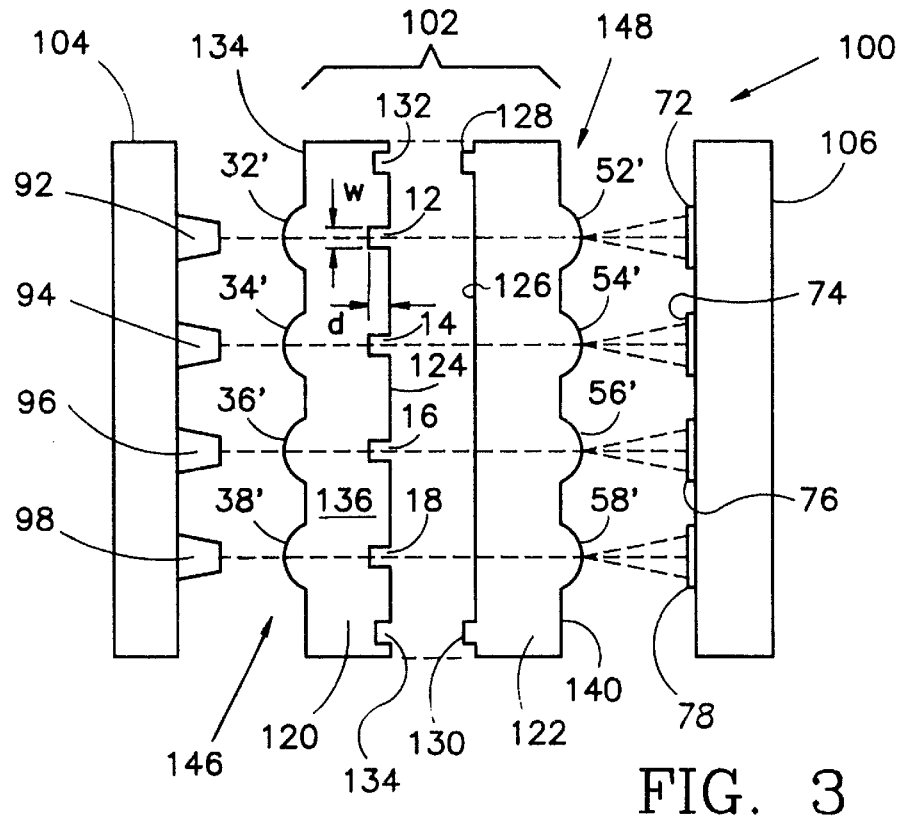
FIG. 3 is an exploded top plan view of a miniaturized optical system in accordance with the present invention.
Figure 4:
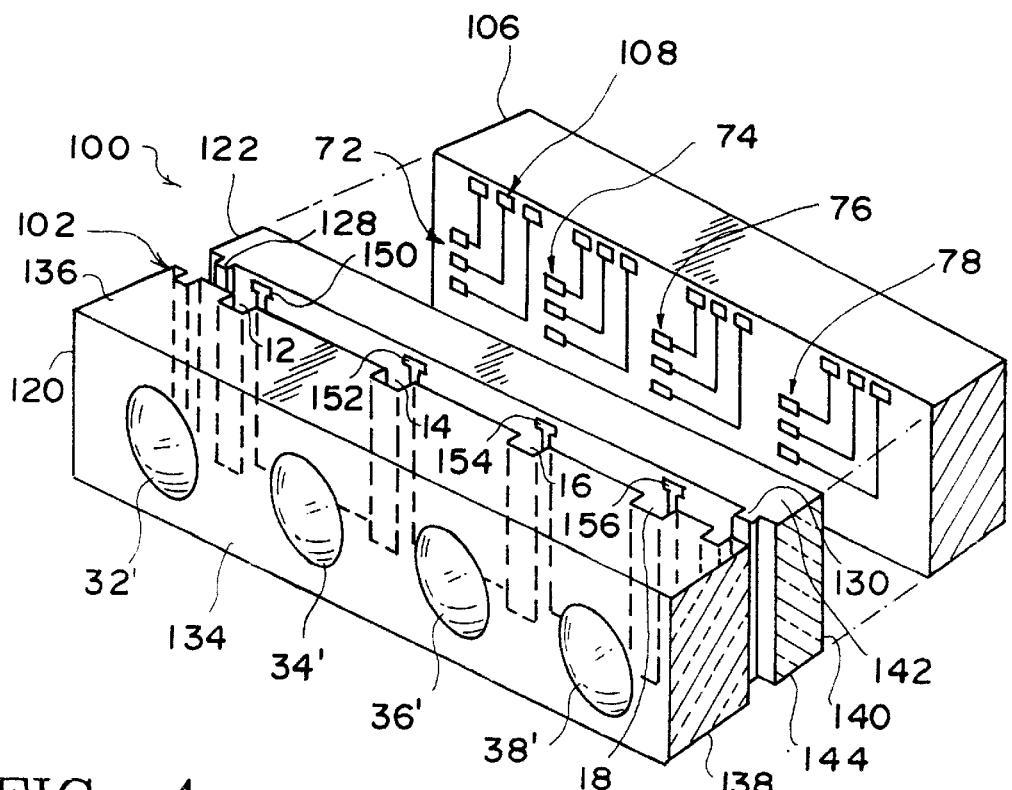
FIG. 4 is a partial top perspective view of the device of FIG. 3, partially exploded.
Figure 5:
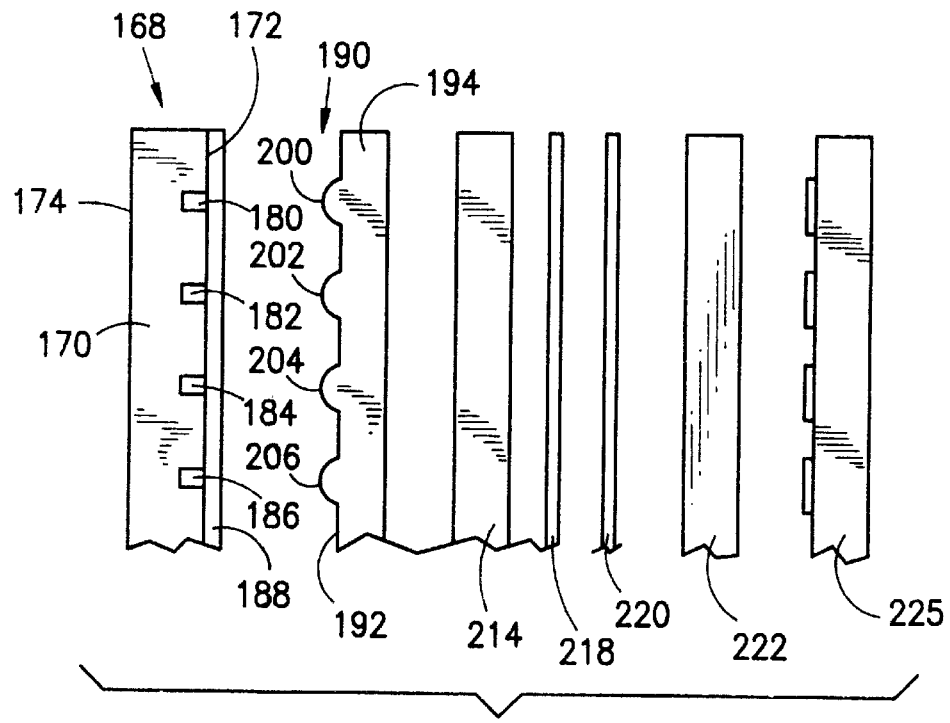
FIG. 5 is a top plan view of a modified form of the optical analysis system of the present invention.

An optical chemical analysis device incorporating the features described above with respect to FIGS. 1 and 2 is illustrated generally at 100 in FIGS. 3, 4, and 5, to which reference is now made. As there illustrated, a two-component carrier block 102 is positioned between an illumination source 104 and an output light detector array 106. The illumination source 104 incorporates the plural lasers 92, 94, 96, and 98, for example, while the detector array 106 incorporates the photo detectors 72, 74, 76 and 78. In a preferred form of the invention, the detector array 106 is a silicon wafer which incorporates on one surface the light sensitive photodetectors, with accompanying signal processing electronics being embedded in the wafer. Alternatively, the detector elements may be connected to suitable surface contact pads, such as those illustrated at 108, for connection to external detector circuitry.

The carrier block 102, in one embodiment of the invention, incorporates a channel block 120 and a mating cover block 122, the channel block containing a large number of miniature parallel sample channels, such as the channels 12, 14, 16 and 18 previously described, fabricated on a planar inner side wall 124. The cover block 122 includes a planar inner side wall 126 opposed to, or facing, the wall 124, with the walls 124 and 126 engaging each other, as illustrated in FIG. 4, when the component blocks 120 and 122 are mated together, so that the cover 122 closes the channels 12, 14, 16, and 18. The cover 122 may be provided with alignment ribs, such as the ribs 128 and 130, which engage corresponding alignment grooves 132 and 134 on the face 124 of channel block 120 to ensure proper alignment of component blocks 120 and 122 when the carrier block 102 is assembled by mating the two components.

In one form of the invention, the blocks 120 and 122 are made of plastic, glass, quartz, or similar optically clear, transparent material. In the illustrated embodiment, each of the blocks 120 and 122 are generally rectangular, with carrier block 120 having a planar outer side wall 134 generally parallel to inner wall 124 and having top and bottom walls 136 and 138. Similarly, cover block 122 includes an outer side wall 140 parallel to inner side wall 126 and further includes top and bottom walls 142 and 144. Channel block 120 preferably incorporates a plurality of lenses, such as the lenses 32, 34, 36 and 38 illustrated diagrammatically in FIG. 2, with one lens provided for each sample channel. These lenses preferably are integrally formed microlenses fabricated in an array 146 on the block 120, as illustrated at 32', 34', 36', and 38' in FIGS. 3 and 4, although it will be understood that individual lenses may be secured to the outer side wall 134, as by an adhesive, or mounted close to wall 134 on a separate holder, if desired. The lenses are optically aligned with respective sample channels 12, 14, 16, and 18 so that sample illuminating light from each of the laser sources 92, 94, 96 and 98 is directed by its corresponding lens to a corresponding sample channel or to a corresponding group of channels.

The cover block 122 also incorporates a plurality of lenses such as the collection lenses 52, 54, 56 and 58 illustrated diagrammatically in FIG. 2. These lenses preferably are integrally formed microlenses fabricated in an array 148 on the block 122 as illustrated at 52', 54', 56', and 58' in FIG. 3, although it will be understood that separate lenses may be secured to the outer side wall 140 of block 122 as by an adhesive, or may be mounted on a suitable holder close to side wall 140, if desired. In a preferred form of the invention, the collection lenses 52', 54', 56' and 58' each incorporate a diffraction grating which divides the output light from each of the sample channels into its separate wavelength components. The collection lenses then direct the different wavelengths of the output light from each sample channel to corresponding detector elements of the detectors 72, 74, 76, and 78 of detector array 106. If desired, a separate diffraction grating or prism can be incorporated between the collection lens array 148 and the detector to provide the required color separation.

It will be understood that the channel block component 120 and the cover block component 122 can be fabricated in a variety of ways. Preferably, however, both of the mating carrier block components are molded to incorporate on outer surfaces 134 and 140 their respective illumination lens array 146 and collection lens array 148, with the inner side wall 124 of block 120 being molded to incorporate the parallel sample channels 12, 14, 16 and 18 and the alignment grooves 132 and 134, and wall 126 of block 122 being molded to incorporate mating ribs 128 and 130. A sample to be analyzed, such as a gel material containing DNA fractions, may then be placed in the sample channel and the cover block mated to the channel block to close the channels. Alternatively, the cover block 122 can be mated to the channel block 120 and the sample material injected into the individual channels. As a further modification, matching channels can be provided on both the channel block and the cover block, with each block then providing a portion of the sample channel depth.

The fabrication of blocks 120 and 122 with miniaturized sample channels and unitary illumination and collection microlenses is carried out using a conventional molding process wherein a two-part die (for example) receives a flowable, optically clear material such as plastic or glass. The die is shaped to define the microlenses, the diffraction grating (if it is to be a unitary part of the collection optics), the sample channels and the mating alignment ribs and grooves. By using a molding process to form the lens arrays and sample channels unitarily, the cost of replicating the system can be significantly reduced.

When the present system is utilized for electrophoretic analysis of a sample, suitable electrodes are provided, for example, on the surface 126 of the cover 122, for contact with the sample material in the channels. Such electrodes are illustrated in FIG. 4 at 150, 152, 154 and 156 as being aligned with the tops of the respective channels 12, 14, 16 and 18, and it will be understood that similar electrodes will be provided at the bottom of each channel. These electrodes are connected to suitable voltage sources as by contacts engaging the electrodes through the respective sample channels.

In electrophoresis of DNA fragments utilizing the optical system of the invention, the DNA fragments are fluorescently labeled before they are placed in the sample channels. A suitable voltage is applied between the top electrodes 150, 152, 154, 156 and corresponding bottom electrodes (not shown) for each channel to produce electrophoretic flow of the sample material in the channels to separate the fragments. Laser light is then directed through the illumination lens array 146 and through block 120 to the respective channels containing the fluorescently labeled DNA fragments, causing the dye to fluoresce. Output fluorescent light from these fragments passes through block 122, is collected by the collection lens array 148 and is directed toward the detector array 106. The various wavelengths of light corresponding to the fluorescent dye outputs are separated by the diffraction gratings or prisms in the collection optics. As previously described, the diffraction gratings can be either separate elements, as illustrated in FIG. 2, or can be a part of the collection lens structure, as illustrated in FIG. 3. The respective wavelengths are directed to corresponding detector elements on detector array 106.

The dimensions of the microlens array of FIGS. 3 and 4 can be extremely small. Each sample channel can have a width w and a depth d, illustrated in FIG. 3 for channel 12, in the range of between about 1 $\mu$m and 1 mm. The corresponding illumination lens on the channel block for each channel may have a diameter on the same order of magnitude; i.e, less than 1 mm, to allow a spacing of about 1 mm between adjacent channels. Similarly, each of the collection lenses carried by the cover 122 has a diameter of less than about 1 mm. This permits a large number of channels with corresponding illumination and collection optics to be placed on a relatively small carrier block to provide a large number of parallel outputs and a significant increase in the speed of the sequencing process. Since each of the channels preferably has its own illumination optics, its own collection optics and its own detector, simultaneous readout of the channels is enabled without the need for scanning the laser source and/or the detector.

Figure 6:
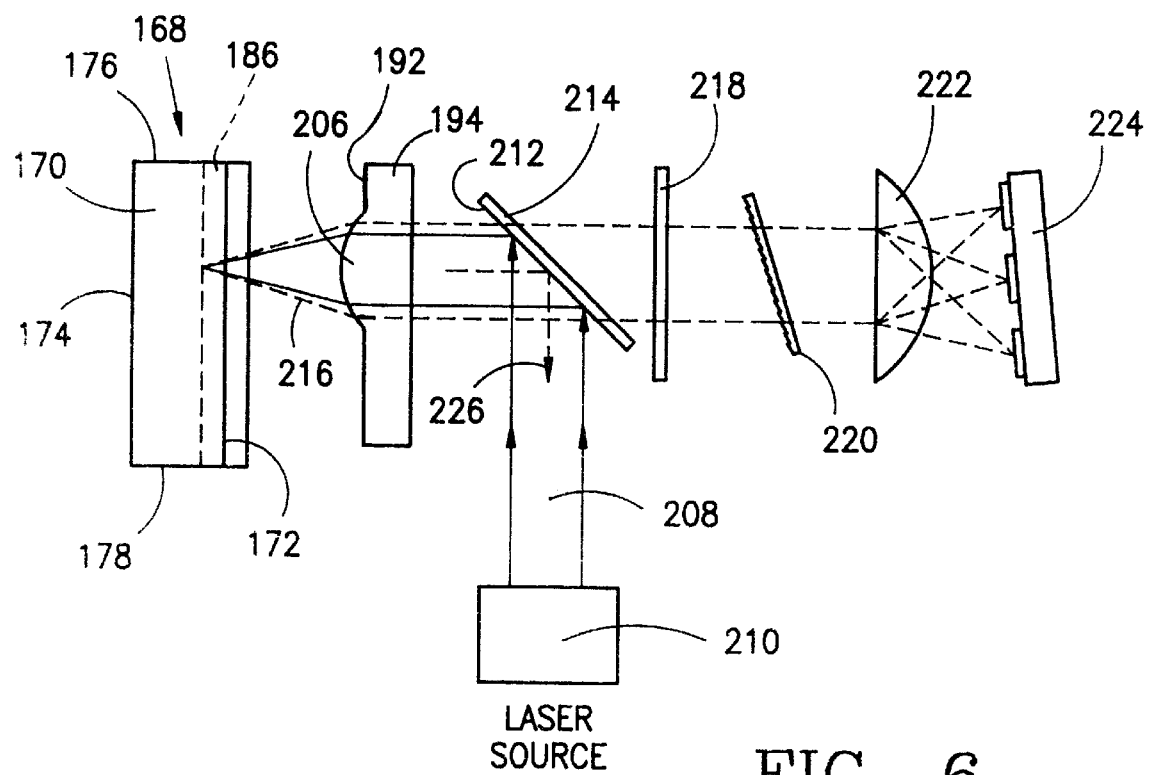
FIG. 6 is a side elevation view of the system of FIG. 5.

A modification of the optical system of the invention is illustrated in FIGS. 5 and 6, to which reference is now made. In this embodiment, a modified two-component carrier block 168 is provided. This block includes a channel block 170 having an inner planar wall 172 and an outer wall 174 generally parallel to wall 172. The channel block includes a top wall 176 and a bottom wall 178 which also are generally parallel to each other. The inner wall 172 incorporates a plurality of sample channels 180, 182, 184, and 186, for example, these channels being similar to the channels 12, 14, 16, and 18 described above and extending from the top wall 176 to the bottom wall 178. Although illustrated as being regularly spaced, linear, and generally parallel, these channels can be grouped or can be irregularly spaced, can be curved, and need not be parallel, if desired.

An optically clear cover block 188 is secured to the inner surface 172 of block 170 to close the channels in the manner described above with respect to cover block 122. In this embodiment, however, neither the channel block 170 nor the cover block 188 incorporates a microlens array. Instead, a microlens array 190 is provided on an inner surface 192 of an optically clear lens block 194 which is spaced from cover block 188 and is generally parallel to wall 172. A separate lens is preferably provided for each of the sample channels, although a single lens can be used with a group of channels, if desired. In the illustrated embodiment, individual lens elements 200, 202, 204 and 206 are aligned with and correspond to sample channels 180, 182, 184 and 186, respectively. The lens array 190 may be integrally formed with the lens block 194 or may be adhesively secured to the surface 192 thereof. Preferably, the block 194 is of glass or plastic and the lenses are integrally molded as a part of the block. It will be understood that, if desired, the cover 122 and the lens block 194 may be combined with the lens array 190 located on the outer surface of the cover in the manner illustrated for array 148 in FIG. 3.

The lens array 190 serves as the illumination lens for a sample material in the channels. As discussed above, the sample may include fluorescent dye-labeled DNA fragments, and the respective sample channels in channel block 170 may incorporate electrodes such as electrode 150 illustrated in FIG. 4 for use in electrophoretic analysis of the sample material. As illustrated in the elevation view of FIG. 6, an illumination beam 208 is directed to the respective channels from a laser source 210, the beam 208 being deflected by a surface 212 of a dichroic mirror 214 through the lens block 194 and through the corresponding lenses such as lens 206 carried by the block 194. The lenses focus the illumination onto their respective electrophoresis channels, as illustrated by channel 186. The illuminating light beam 208 causes the dye-labeled DNA fragments to fluoresce, with the resulting output light 216 due to the fluorescence being collected by the same lens array 190. The array directs the output light through lens block 194, through the dichroic mirror 214, and through a filter 218 to a diffraction device 220 such as a grating or prism. The output light beam 216 is separated by wavelength at grating 220 and passes through a cylindrical focussing lens 222 which directs the light onto corresponding detector elements of detector array 224, which is similar to detector 106. Laser illumination light which is reflected from the sample is indicated by arrow 226. This light is deflected out of the system by dichroic mirror 214, so it does not interfere with the collection optics, but it can also be measured, if desired, to determine the reflectivity of the sample.

In a preferred form of the invention, each of the sample channels, such as channels 12 and 14 illustrated in the enlarged view of FIG. 7, contain a highly porous medium for sample separation in electrophoretic analysis. This porous medium functions as an artificial gel for the sample, and is comprised of a multiplicity of closely spaced, generally parallel pillars, such as the pillars 230 illustrated in FIG. 7, which extend the full depth d of the sample channels.

In the case where the channel block 120 is silicon dioxide, which is optically transparent, the channels and their pillars 230 may be fabricated by the photolithographic dry etch process illustrated in FIGS. 8–11. In that process, a surface 124 of block 120 is covered by an etch resistant coating 232, which may be a thin film of aluminum. The locations of the channels 12, 14, and 16 and of the pillars 230 are photolithographically defined in the etch resistant coating 232 to form an etch mask generally indicated at 234 in FIG. 9. Thereafter, a dry anisotropic ion etch, indicated by arrows 236, is used to etch vertically around the mask 234 to produce the channels 12, 14, and 16 and their included vertical pillars 230, as illustrated in FIG. 10. Thereafter, the etch mask is removed, as illustrated in FIG. 11, and the channels are covered by an encapsulating layer 238 to enclose the channels 12, 14, and 16. Alternatively, the cover block illustrated at 122 or at 188 may be used for this purpose.

Figure 12:
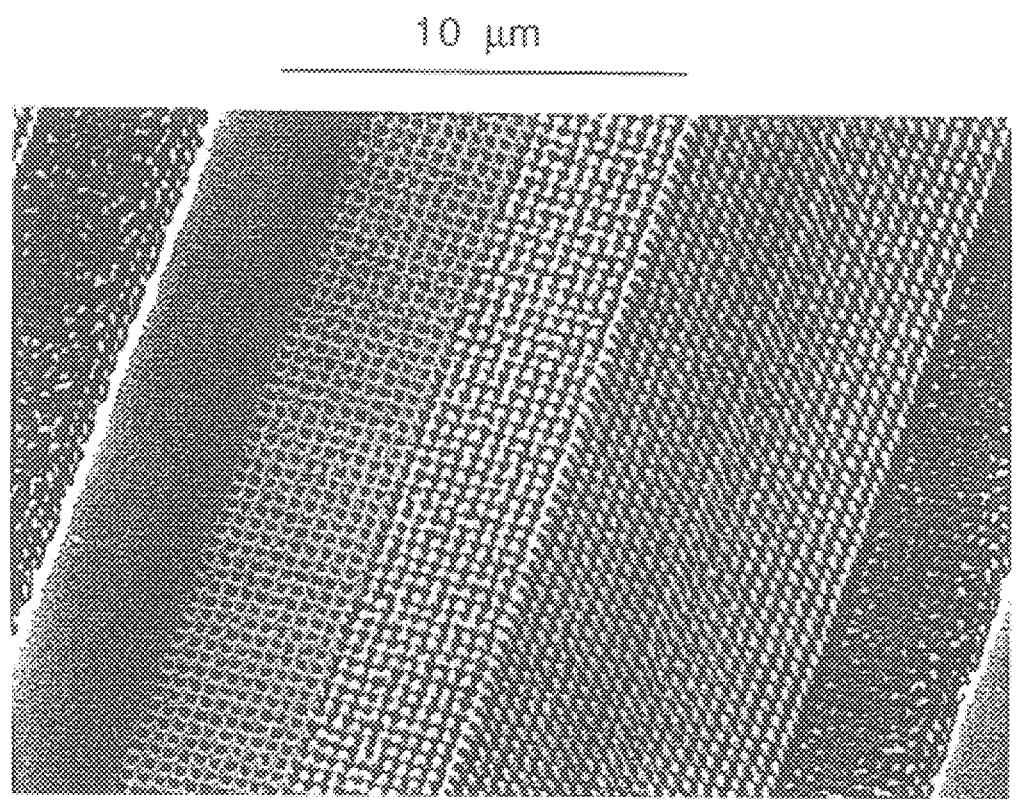
FIG. 12 is a scanning electron micrograph of an artificial gel test structure fabricated by the process of FIGS. 8–11.

As illustrated in the photomicrograph of FIG. 12, the pillars 230 can be fabricated in channels of any desired dimension, the channels in FIG. 12 being on the order of 20 $\mu$m wide, although a channel on the order of 1 $\mu$m wide is preferred. The use of scanning electron beam lithography to define the etch mask 234, illustrated in FIGS. 9 and 10, allows definition of arrays of pillars in silicon, silicon dioxide and other substrates. The pillars may be cylindrical or may have other regular or irregular cross-sectional shapes, and may be spaced in regular columns and rows along the length and width of the channel, or may be irregularly or randomly spaced. This combination of electron beam lithography with thin film mask formation and anisotropic ion etching is used to fabricate arrays of columnar, pillar-shaped, artificial gel structures with diameters as small as about 20 nm, with heights equal to the depth of the channels in which they are located, and with spacings which may average about 20 nm between adjacent pillars.

In a preferred form of the described process, electron beam lithography is used with a polymethomethacrilate resist layer to pattern the aluminum mask 232, which is on a silicon dioxide substrate 120, using a $Cl_2/BCl_3/CH_4$ reactive ion etch. The aluminum mask pattern is transferred into the silicon dioxide substrate by reactive ion etching in a magnetically confined $CHF_3$ plasma. This process has been used to create a range of sizes of pillars along the length of a channel, the different sizes being used to vary the density and function of the artificial gel material, thereby to varying its refractive index.

It is noted that image resolution in electron beam lithography is not limited by the wavelength of light, but does have a resolution that is limited by the ability to focus the beam and by the lateral straggle of secondary electrons. This is a fundamental limit to electron beam lithography and is on the order of 5 nm for energetic electron beams in polymeric resists. In the foregoing process, a finely focused electron beam is scanned under computer control to expose the polymeric resist which is developed in a solvent that selectively removes the exposed areas. The polymer is then used as a sacrificial mask for the patterning of a durable etch-resistant material such as aluminum. A directional reactive ion etch is then used, as described with respect to FIG. 10, to transfer this pattern into the substrate of interest.

Figure 13:
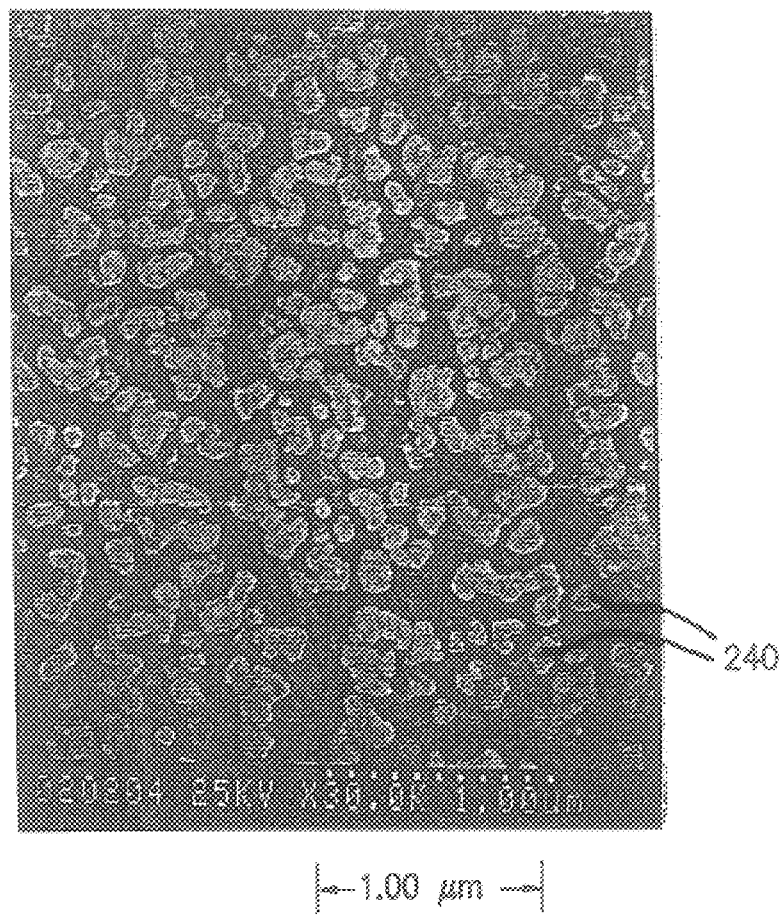
FIG. 13 is a scanning electron micrograph top view of an artificial gel structure fabricated by a thin film mask and reactive ion etching.
Figure 14:
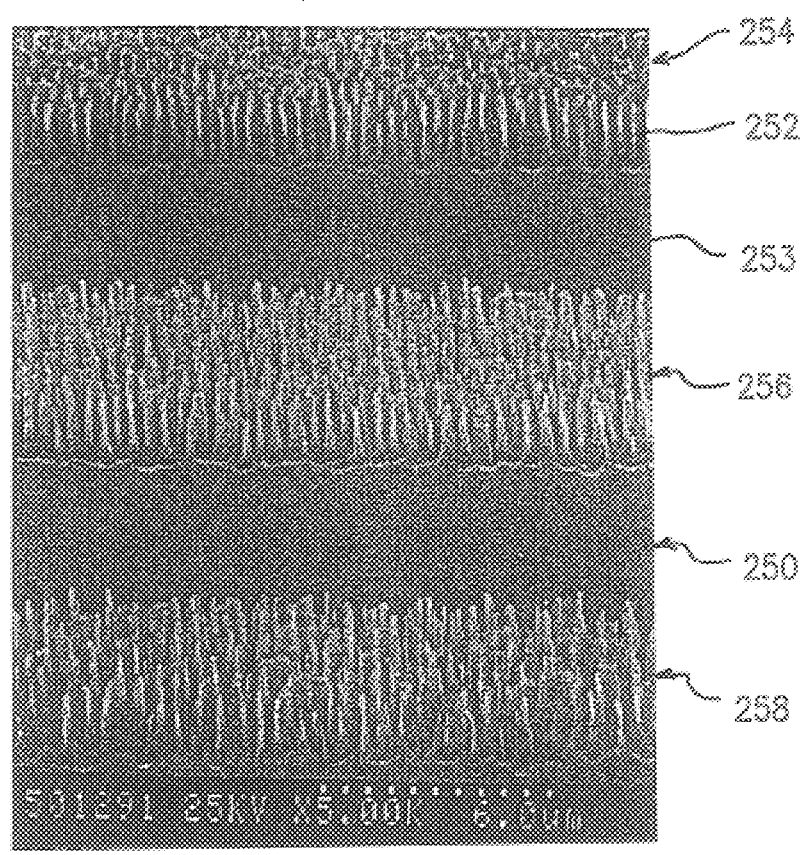
FIG. 14 is a scanning electron micrograph of plural artificial gel structures fabricated by electron beam exposure of a polymer.

An alternative to the electron beam lithography process described above is a thin film process in which a thin metallic film of gold, nickle, tin or other material capable of withstanding reative ion etching processes is deposited on a nonwetting surface as illustrated in FIGS. 13 and 14. This thin film beads up on the nonwetting surfa to form isolated islands on the surface, with the size and spacing of the islands being controlled by the deposition temperature, thickness and other deposition parameters. This process produces islands which can have dimensions as small as about 10 nm, with spacings between adjacent islands of about 10 nm. Thereafter, reactive ion etching may be used to transfer the mask pattern into the substrate to produce a random array of pillars. The resulting array is illustrated in FIG. 13, which is a top plan view of a multiplicity of pillars 240, having random shapes and varying sizes and spacings formed from the thin film mask defined above.

Structures having an array such as that illustrated in FIG. 13 have been produced in silicon dioxide, silicon, germanium, polymers and metals. In one example, pillars were etched 400 nm deep into silicon by $Cl_2$ reactive ion etch, with the pillar size and separation being approximately 100 nm. The size, shape and spacing of these pillars, when used as an artificial gel material, affects the DNA motion in the sequencing of DNA fragments.

The channel blocks 120 or 170 preferably are made of an optically clear plastic or glass material fabricated in a master die mold shaped to incorporate the lens arrays and sample channels described above. The master mold may also be shaped to produce the artificial gel structure within the channels so that the channel blocks can be easily replicated from the mold. In addition, corresponding molds may be provided for fabricating the microlenses 52', 54', 56' and 58' on cover block 122 and lenses 200, 202, 204 and 206 on lens block 194.

A master mold for producing the artificial gel structure can be produced, for example, by modifying the etch mask illustrated in FIG. 9 to permit etching away the substrate in the region of the islands 242 (FIG. 10) between the channels in which the pillars 230 are located, thereby producing the die structure of FIG. 14. As there illustrated, a substrate 250 carries a plurality of upstanding pillars 252 arranged in linear, or channelized, arrays on, and extending upwardly from, the surface 253 of substrate 250, as generally indicated at 254, 256 and 258.

Figure 15:
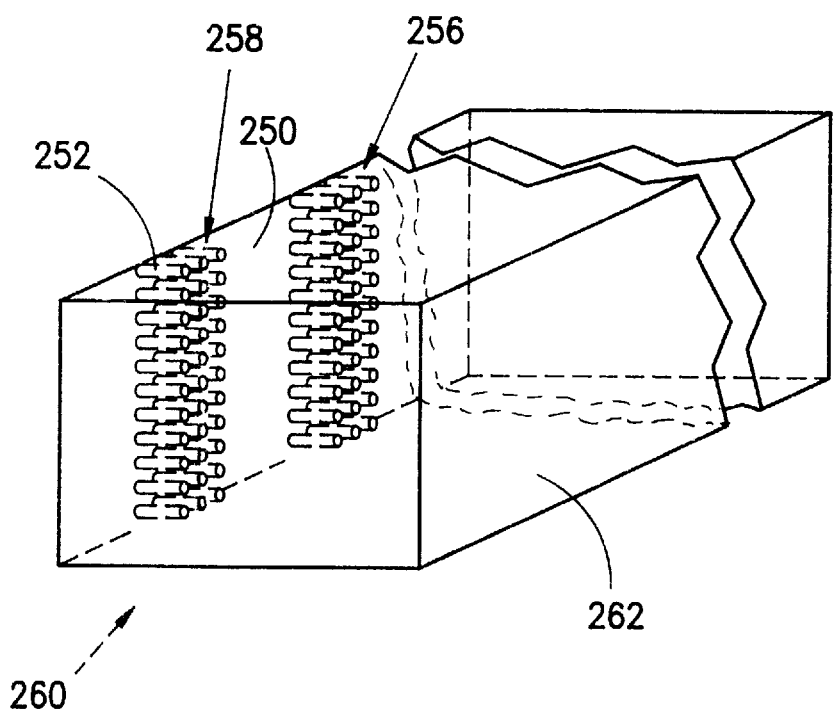
FIG. 15 diagrammatically illustrates a die mold used to produce a block having microfabricated flow channels incorporating an artificial gel.

The linear arrays 254, 256, 258 of closely spaced pillars 252 may be incorporated as one wall of a die mold 260, as diagrammatically illustrated in FIG. 15, with the columns 252 extending into the interior of mold 260. This mold forms a master for the production of a block having channels such as channels 12 and 14 in FIG. 7 with the channels incorporating an artificial gel. A moldable plastic material may then be poured into the mold 260 to fill the mold and the spaces between pillars 252. When the plastic cures, wall 262, for example, of the mold may be removed to permit removal of a channel block such as that illustrated at 170 which incorporates the channels 12, 14, etc., incorporating artificial gel structure columns 230 formed between the die pillars 252 in a reverse pattern. In this way, the channel block 170 can be replicated from the master for inexpensive, rapid production of channel blocks incorporating channels containing a gel structure.

If desired, the wall 262 of mold 260 may contain shaped cavities for formation of the microlenses 32', 34', etc., whereby the channel block 120 can be fabricated in mold 260.

As previously explained, a sample material to be analyzed may be placed in the channels, with the porous gel structure allowing particles of different sizes to flow through the channel at different rates for separation of the particles. A cover block 122 or other suitable cover is placed over the channels and the carrier block is inserted in the described optical system of FIG. 3 or of FIG. 5 for optical analysis of the sample. The optical system provides illumination of the sample material in the channels by arrays of lenses and/or mirrors to direct and focus the light onto the sampling regions of the channels. Additional arrays of microoptical mirrors, prisms or gratings, and lenses spectrally resolve and focus output light from the sample onto a suitable detector array. The illuminating laser light is transmitted through, refracted by, or reflected by, or may cause fluorescence in, the material to be analyzed, with the resulting output light indicating properties of the sample material.

The illuminating light can be from a pulsed or a continuous wave laser source, with continuous wave light having the advantages of increased observation time, an absence of stimulated Raman emissions, and ease of eliminating stray laser light from the detection system. Pulsed laser excitation offers maximum fluorescent emission rates for superior photon collection during the period of excitation, but produces intense background emission that must be minimized, as by grating the detectors.

A single laser source may be used, with the lens array being illuminated by an expanded beam and the beam being divided and focused simultaneously onto the array of sample channels at the focus of the illumination optics. Alternatively, a single laser source can be scanned across the illumination lens array to sequentially impinge on single channels or groups of channels. Another alternative is to form multiple laser beams, with one beam incident on each illumination lens element to excite a single sample channel or a group of channels at the focus of each lens.

A significant feature of the present design is that it does not require mechanically movable optics, allowing rigid alignment of the components and use of a high numerical aperture lenses for collecting maximum light, with short focal lengths to provide a compact system and a dense array of components. The low cost and ease of fabrication of the optics and the sample channels permit disposal of the channel blocks after so as to prevent contamination from one test to the next.

In its use in DNA sequencing, the present invention provides a significant increase in the speed of the sequencing process by providing a higher degree of parallelism in the sample channels as a result of the large number of closely-spaced channels that can be fabricated. The channels can be fabricated with artificial gel structures to eliminate the need for filling them with hard-to-handle liquid gels, thus reducing the time for conducting a sequencing operation as well as reducing the cost. The system is miniaturized, and thus requires smaller volumes of DNA material, and is less expensive since the artificial gel structure can be formed by processes which permit easy replication. The artificial gel material is controllable and reproducible, making measurements more reliable, and the channels are easily integrated into a highly parallel microlens optical system for fluorescence detection.

Although the invention has been described in terms of a preferred embodiments, it will be apparent to those of skill in the art that numerous variations and modifications can be made without departing from the true spirit and scope thereof as set forth in the following claims.

What is claimed is:

1. A microoptical system comprising:

a plurality of closely-spaced, elongated, generally parallel, coplanar micron-scale sample channels;

an artificial gel material comprising a multiplicity of pillar structures having diameters of about 20 nm in each said channel;

an illumination source providing illuminating light;

illumination optics directing illuminating light from said source to said sample channels to produce corresponding sample output beams;

a detector array; and collection optics directing said output beams to corresponding detector elements of said detector array.

2. The optical system of claim 1, wherein each said channel has a width of about 1 µm.

3. The optical system of claim 1, wherein said pillar structures are spaced apart by about 20 nm.

4. The optical system of claim 3, wherein said illumination optics includes a channel block having a first surface which incorporates said sample channels.

5. The optical system of claim 4, wherein said channel block is replicated from a die mold having channelized gel assembly arrays corresponding to said sample channels and included artificial gel structure.

6. The optical system of claim 4, wherein said channel block is optically clear and has a second surface parallel to said first surface, and wherein said illumination optics includes microlenses located on said second surface in alignment with corresponding sample channels.

7. The optical system of claim 6, wherein each said microlens directs illuminating light through said channel block to a corresponding channel.

8. The optical system of claim 4, wherein said illumination optics further includes an optically clear lens block having a plurality of microlenses for directing said illumination light to said channels, said output beams being directed through said microlenses to said collection means.

9. The optical system of claim 4, further including a cover block having a first surface engaging said first surface of said channel block to enclose said channels.

10. The optical system of claim 9, wherein said cover block includes a second surface spaced from said first surface and wherein said collection optics is located on said cover block second surface.

11. The optical system of claim 10, wherein said collection optics includes a plurality, of collection microlenses aligned with corresponding channels.

12. The optical system of claim 9, wherein said illumination optics includes a lens block having a plurality of microlenses for directing said illumination to said sample channels, said output beams being directed through said microlenses to said collection means.

13. The optical system of claim 12, wherein said collection optics includes a collection lens.

14. The optical system of claim 13, wherein said collection optics further includes a diffraction grating.

15. The optical system of claim 12, further including a dichroic mirror directing light from said illumination source to said illumination optics and directing output beams, from said sample channels to said collection optics.

16. The optical system of claim 4, further including electrodes for supplying a voltage to sample material in said sample channels for electrophoresis.

17. A microoptical system comprising:
a plurality of closely-spaced, elongated, generally parallel, coplanar micron-scale sample channels formed in a substrate, each said channel having a floor and spaced, vertical walls;
a multiplicity of closely-spaced, vertical pillars on said floor of at least one channel, said pillars each having a cross-sectional dimension of about 20 nm to provide an artificial gel for sample analysis;
an illumination source providing illuminating light;
illumination optics directing illuminating light from said source to said sample channels to Produce corresponding sample output beams;
a detector array; and
collection optics directing said output beams to corresponding detector elements of said detector array.

18. The optical system of claim 17, wherein said channel has a width of about 1 μm, and wherein said pillars are randomly spaced in said channel to provide a porous path through said channel for said sample material.

19. The optical system of claim 18, wherein said substrate and pillars are optically clear to permit optical analysis of said sample material.

20. The optical system of claim 19, wherein said substrate and pillars are a unitary molded plastic material.

21. The optical system of claim 17, wherein said pillars are irregularly spaced within said channel.

22. The optical system of claim 17, wherein said pillars have generally cylindrical cross-sections.

23. The optical system of claim 17, wherein said pillars are regularly spaced within said channel.

24. The optical system of claim 17, wherein said pillars have non-cylindrical cross sections with diameters of about 20 nm.

25. The optical system of claim 17, wherein said pillars have an average spacing between adjacent pillars of about 20 nm.

26. An optical system for chemical analysis of sample material in a porous medium, comprising:
a replaceable optically clear channel block having first and second parallel surfaces;
at least one microfabricated micron-scale sample channel on said first surface, said channel including an integral porous medium;
at least one illuminating lens integral with said second surface of said channel block and aligned with a corresponding sample channel;
an optically clear cover for said channel;
illuminating light directed through said at least one lens and said channel block and being focused on said corresponding sample channel;
a detector; and
collection optics including at least one collector lens aligned with said corresponding sample channel for directing light from said channel to said detector, said illuminating lens and said collector lens having short focal lengths to provide a compact system for analysis.

27. The system of claim 26, wherein said illuminating light is produced by a plurality of sources of laser light.

28. The system of claim 26, wherein said integral porous medium is an artificial gel consisting of a multiplicity of closely-spaced, parallel pillars.

29. The system of claim 28, wherein said pillars have diameters of about 20 nm and are spaced about 20 nm apart.

30. The system of claim 29, wherein said pillars are spaced at varying distances to separate sample material flowing through said channels.

31. An optical system for chemical analysis of sample material in a porous medium, comprising:
a replaceable channel block having a first surface;
at least one microfabricated sample channel on said first surface;
a porous medium in and integral with said channel;
an optically clear cover for said channel;
at least one illuminating lens directing light through said cover to said sample channel;
a detector; and
collection optics including at least one collector lens aligned with said sample channel for directing light from said channel to said detector for detecting light produced by a sample material in said porous medium.

32. A microoptical system, comprising:
an optically transparent carrier block incorporating at least one channel for receiving a sample material;
an illumination lens integral with said carrier block and located to direct light to said channel; and
a collector lens integral with said carrier block and located to direct light received from said channel to a detector.

33. The system of claim 32, wherein the optical path through said illumination lens, through said channel and through said collector lens is about 1 cm in length.

34. The system of claim 32, wherein said carrier block comprises:
a channel block having spaced first and second surfaces, said block carrying said channel on said first surface and said illumination lens on said second surface; and
a cover block having first and second surfaces, said first surface of said cover block engaging said first surface of said channel block to provide a cover for said channel, said second surface carrying said collector lens.

35. The system of claim 32, wherein said carrier block incorporates a multiplicity of spaced, generally parallel channels, said illumination lens directing light to illuminate said channels.

36. The system of claim 35, further including a plurality of illuminating lenses integral with said carrier block and aligned with corresponding channels.

37. The system of claim 36, further including a plurality of collector lenses integral with said carrier block and aligned with corresponding channels.

38. The system of claim 37, wherein said carrier block comprises a channel block which includes said sample channels and a cover block, said illuminating lenses being integral with said channel block and said collector lenses being integral with said cover block.

39. The system of claim 38, further including diffraction means adjacent said collector lenses.

40. The system of claim 39, wherein each said channel includes an artificial gel structure.

41. The system of claim 40, further including electrodes in said carrier block for producing an electric field in said channels.

42. The system of claim 37, wherein said illuminating lenses and said collector lenses are on one surface of said carrier block.

43. The system of claim 37, wherein said illuminating lenses and said collector lenses are on opposite sides of said carrier block.

* * * * *